(12) United States Patent
Mansfield et al.

(10) Patent No.: US 10,729,621 B2
(45) Date of Patent: Aug. 4, 2020

(54) ACOUSTIC REFLECTOMETRY DEVICE IN CATHETERS

(71) Applicant: SonarMed Inc., Carmel, IN (US)

(72) Inventors: Jeffrey Mansfield, Bloomington, IN (US); Laura L. Lyons, Carmel, IN (US)

(73) Assignee: SONARMED INC., Carmel, IN (US)

( * ) Notice: Subject to any disclaimer, the term of this patent is extended or adjusted under 35 U.S.C. 154(b) by 385 days.

(21) Appl. No.: 15/610,360

(22) Filed: May 31, 2017

(65) Prior Publication Data
US 2017/0340522 A1 Nov. 30, 2017

Related U.S. Application Data

(60) Provisional application No. 62/343,476, filed on May 31, 2016.

(51) Int. Cl.
*A61J 15/00* (2006.01)
*A61B 7/00* (2006.01)
(Continued)

(52) U.S. Cl.
CPC ........... *A61J 15/0088* (2015.05); *A61B 7/00* (2013.01); *A61B 7/008* (2013.01); *A61B 7/023* (2013.01);
(Continued)

(58) Field of Classification Search
CPC ...... A61J 15/00; A61J 15/0003; A61J 15/008; A61J 15/0088; A61B 7/00; A61B 7/008; A61B 7/023; A61B 8/12; A61B 90/06
See application file for complete search history.

(56) References Cited

U.S. PATENT DOCUMENTS

| 2,209,944 A | 7/1940 | Walker |
| 4,344,436 A | 8/1982 | Kubota |

(Continued)

FOREIGN PATENT DOCUMENTS

| EP | 1166813 A2 | 1/2002 |
| WO | WO-2004045404 A1 | 6/2004 |

(Continued)

OTHER PUBLICATIONS

"Boque, et al., Endotracheal tube intraluminal diameter narrowing after mechanical ventilation: use of acoustic reflectometry, Springer-Verlarg, Intensive Care Med, 2004, 30:2204-09."

(Continued)

*Primary Examiner* — Joseph D. Boecker
(74) *Attorney, Agent, or Firm* — FisherBroyles, LLP

(57) ABSTRACT

A device and method for verifying the proper position of catheters in the body by means of acoustic reflectometry, the device including a sound source, one or more sound receivers, a tube with compliant walls and open distal end to be introduced through an entrance to a body cavity, the sound source and receiver(s) coupled to the proximal end of the tube, a processor for causing the sound source to generate an acoustic excitation signal, the processor processing the acoustic signals sensed by the sound receiver(s) and generating an approximation of the acoustic impulse response of the tube, and the processor analyzing the acoustic impulse response to determine the position of the tube in the body cavity.

21 Claims, 6 Drawing Sheets

(51) Int. Cl.
  *A61B 8/12* (2006.01)
  *A61B 7/02* (2006.01)
  *A61B 90/00* (2016.01)
(52) U.S. Cl.
  CPC .......... *A61B 8/12* (2013.01); *A61B 2090/062* (2016.02); *A61J 15/0003* (2013.01)

(56) References Cited

U.S. PATENT DOCUMENTS

| | | | |
|---|---|---|---|
| 4,501,273 A | | 2/1985 | McGinnis |
| 4,630,606 A | | 12/1986 | Weerda et al. |
| 4,697,593 A | | 10/1987 | Evans et al. |
| 4,700,396 A | | 10/1987 | Bolin |
| 5,445,144 A | * | 8/1995 | Wodicka ............ A61M 25/0105 |
| | | | 128/207.14 |
| 5,575,310 A | | 11/1996 | Kamen et al. |
| 5,655,518 A | | 8/1997 | Burden |
| 5,666,960 A | | 9/1997 | Fredberg et al. |
| 5,823,965 A | * | 10/1998 | Rasmussen ............ A61B 5/085 |
| | | | 600/462 |
| 5,853,005 A | | 12/1998 | Scanlon |
| 6,257,234 B1 | | 7/2001 | Sun |
| 6,390,091 B1 | | 5/2002 | Banner et al. |
| 6,443,907 B1 | | 9/2002 | Mansy et al. |
| 6,629,527 B1 | | 10/2003 | Estes et al. |
| 6,705,319 B1 | * | 3/2004 | Wodicka ............ A61M 16/0488 |
| | | | 128/200.26 |
| 7,691,070 B2 | | 4/2010 | Comanducci |
| 7,891,354 B2 | | 2/2011 | Farbarik |
| 8,038,629 B2 | | 10/2011 | Solanki et al. |
| 8,152,751 B2 | | 4/2012 | Roger et al. |
| 8,280,489 B2 | | 10/2012 | Li et al. |
| 8,371,303 B2 | | 2/2013 | Schaner et al. |
| 8,394,031 B2 | | 3/2013 | Mansy et al. |
| 8,424,529 B2 | | 4/2013 | Efrati et al. |
| 8,522,787 B2 | | 9/2013 | Lin et al. |
| 8,608,658 B2 | | 12/2013 | Burbank et al. |
| 8,611,984 B2 | | 12/2013 | Greenburg et al. |
| 8,764,725 B2 | | 7/2014 | Averbuch |
| 8,844,534 B2 | | 9/2014 | Behlmaier |
| 8,905,029 B2 | | 12/2014 | Colburn |
| 9,364,180 B2 | | 6/2016 | Armitstead |
| 9,498,590 B2 | | 11/2016 | Mansfield et al. |
| 9,707,363 B2 | | 7/2017 | Mansfield et al. |
| 2001/0004893 A1 | | 6/2001 | Biondi et al. |
| 2002/0016610 A1 | | 2/2002 | Hovanes et al. |
| 2003/0034035 A1 | * | 2/2003 | Raphael ............ A61M 16/0488 |
| | | | 128/207.14 |
| 2005/0005935 A1 | | 1/2005 | Gradon |
| 2006/0070623 A1 | | 4/2006 | Wilkinson et al. |
| 2006/0070624 A1 | | 4/2006 | Kane et al. |
| 2006/0081255 A1 | | 4/2006 | Miller et al. |
| 2006/0107962 A1 | | 5/2006 | Ward et al. |
| 2007/0137652 A1 | | 6/2007 | Qureshi et al. |
| 2007/0257788 A1 | | 11/2007 | Carlson et al. |
| 2008/0078248 A1 | | 4/2008 | Farbarik |
| 2008/0078390 A1 | | 4/2008 | Milne et al. |
| 2009/0025728 A1 | | 1/2009 | Aljuri et al. |
| 2009/0082676 A1 | | 3/2009 | Bennison |
| 2009/0099479 A1 | | 4/2009 | Solanki et al. |
| 2009/0120439 A1 | | 5/2009 | Goebel |
| 2009/0187164 A1 | * | 7/2009 | Rowe ................ A61M 25/0105 |
| | | | 604/529 |
| 2009/0229605 A1 | | 9/2009 | Efrati et al. |
| 2009/0229611 A1 | | 9/2009 | Martin et al. |
| 2009/0301601 A1 | | 12/2009 | Enerson et al. |
| 2009/0318805 A1 | | 12/2009 | Raphael |
| 2010/0252048 A1 | | 10/2010 | Young et al. |
| 2010/0261996 A1 | | 10/2010 | Li et al. |
| 2010/0305503 A1 | * | 12/2010 | Fang ...................... A61B 1/042 |
| | | | 604/96.01 |
| 2011/0030694 A1 | | 2/2011 | Schaner et al. |
| 2011/0087123 A9 | | 4/2011 | Choncholas et al. |
| 2011/0154241 A1 | | 6/2011 | Skidmore et al. |
| 2011/0197885 A1 | | 8/2011 | Wondka et al. |
| 2011/0197888 A1 | | 8/2011 | Deutsch et al. |
| 2011/0313689 A1 | | 12/2011 | Holley et al. |
| 2012/0132211 A1 | | 5/2012 | Halperin et al. |
| 2012/0232411 A1 | | 9/2012 | Brunner et al. |
| 2013/0098363 A1 | | 4/2013 | Forte et al. |
| 2013/0228171 A1 | | 9/2013 | Mansfield et al. |
| 2013/0255691 A1 | * | 10/2013 | Mansfield ............. A61M 16/04 |
| | | | 128/207.14 |
| 2013/0281885 A1 | | 10/2013 | Rowbottom et al. |
| 2014/0051989 A1 | | 2/2014 | McGowan et al. |
| 2014/0058253 A1 | | 2/2014 | Prough et al. |
| 2014/0155720 A1 | | 6/2014 | Stanislaus et al. |
| 2014/0249428 A1 | | 9/2014 | Ingold, Jr. et al. |
| 2014/0366874 A1 | | 12/2014 | Deutsch et al. |
| 2016/0279366 A1 | | 9/2016 | Mansfield et al. |
| 2017/0043110 A1 | | 2/2017 | Mansfield et al. |
| 2017/0281887 A1 | | 10/2017 | Mansfield et al. |

FOREIGN PATENT DOCUMENTS

| | | | | |
|---|---|---|---|---|
| WO | WO-2009149351 A1 | | 12/2009 | |
| WO | WO-2010141415 A1 | | 12/2010 | |
| WO | WO-2013134166 A1 | | 9/2013 | |
| WO | WO-2013149138 A1 | | 10/2013 | |
| WO | WO-2016154607 A1 | | 9/2016 | |
| WO | WO-2016190807 A1 | * | 12/2016 | ............... A61B 5/06 |
| WO | WO-2017210353 A1 | | 12/2017 | |

OTHER PUBLICATIONS

"Schumann, et al., Detection of partial endotracheal tube obstruction by forced pressure oscillations, Respiratory Physiology & Neurobiology 155 (2007), 227-233."
Co-pending U.S. Appl. No. 15/610,360, filed May 31, 2017.
Co-pending U.S. Appl. No. 16/054,734, filed Aug. 3, 2018.
"Extended European search report and opinion dated Nov. 17, 2015 for EP Application No. 13770312.0".
"Fiastro, et al., Pressure Support Compensation for Inspiratory Work due to Endotracheal Tubes and Demand Continuous Positive Airway Pressure, Chest, Mar. 1988, 93(3):499-505."
"International Preliminary Report on Patentability written opinion dated Jul. 11, 2013 for PCT Application No. US 2013034599".
"International Preliminary Report on Patentability written opinion, International search report and written opinion dated Jun. 24, 2016 for PCT Application No. US-2016024380".
"International search report and written opinion dated Jul. 9, 2013 for PCT Application US-2013028957".
"International search report and written opinion dated Aug. 10, 2017 for PCT Application No. US-2017035299".
"Notice of allowance dated Mar. 10, 2017 for U.S. Appl. No. 13/853,252."
"Notice of allowance dated Jul. 21, 2016 for U.S. Appl. No. 13/783,916".
"Office action dated Feb. 4, 2016 for U.S. Appl. No. 13/853,252."
"Office action dated Jun. 11, 2015 for U.S. Appl. No. 13/783,916".
"Office action dated Aug. 15, 2016 for U.S. Appl. No. 13/853,252".
"Office action dated Aug. 27, 2015 for U.S. Appl. No. 13/853,252".
"Office action dated Nov. 25, 2015 for U.S. Appl. No. 13/783,916".
"U.S. Appl. No. 15/336,186 Notice of Allowance dated Apr. 27, 2018".
EP17807434.0 Extended Search Report dated Nov. 12, 2019.

* cited by examiner

ACOUSTIC REFLECTOMETRY DEVICE IN CATHETERS

CROSS-REFERENCE

This application claims the benefit of U.S. Provisional Application No. 62/343,476, filed May 31, 2016, which application is incorporated herein by reference.

BACKGROUND OF THE INVENTION

Nasogastric enteral access devices (for example, NG-EADs, enteral feeding tubes, nasogastric tubes, NG tubes, feeding tubes) are widely used in patients who require nutrition to be delivered directly to the stomach due to an inability to swallow foods on their own. For example, a patient who is being mechanically ventilated through an endotracheal tube (ETT) requires an NG tube because the ETT prevents the patient from swallowing without the risk of food being aspirated into the airways.

When properly positioning an NG tube in a patient, the tube tip is inserted through the nose into the esophagus and advanced into the stomach or farther into the duodenum. To confirm proper placement, a variety of methods are used according to the prior art, including chest x-rays and testing of aspirates for a pH reading between 1 and 5.5. However, errors in placement still occur either due to misinterpretation of the results (e.g. misreading of chest x-ray), unintentionally introducing substances in the NG tube that may cause false positive pH readings (flushing tube with water prior to placement), or failing to positively confirm placement in the first place. Accidental placement of the NG tube into the airway also is an ongoing concern and can lead to catastrophic consequences when fluids that are intended for the stomach are delivered directly into the lungs. This aspiration of fluids into the lungs frequently leads to pneumonia which carries risk of serious and potentially lethal complications. Accordingly, there is a need for an improved method and system for assisting in the proper placement of NG tubes.

Several apparatuses and methods for acoustically guiding, positioning, and monitoring tubes within a body are known. See, for example, U.S. Pat. Nos. 5,445,144 and 6,705,319 to Wodicka et al., the disclosure of which is incorporated herein by reference, which disclose an apparatus and method for acoustically monitoring the position of a tube (e.g., ETT) within an anatomical conduit. In various embodiments, a sound pulse is introduced into a wave guide and is recorded as it passes by one or more microphones located in the wave guide wall. As the sound pulse is propagating down the tube, reflected sound pulses arise from changes in cross-sectional area due to constrictions that may exist in the tube. The sound pulse is then emitted through the distal tip of the ETT into the airway (or wherever in the body the tip of the ETT is located) and an acoustic reflection propagates back up the ETT to the wave guide for measurement by the same microphone(s). The amplitude and the polarity of the incident and reflected sound pulse are used to estimate the characteristics of the airway and the ETT, and thereby guide the ETT placement or monitor the ETT for patency.

Another apparatus and method for examination and measurement of constrictions of passages in a cavity by means of acoustic reflectometry is described in U.S. Pat. No. 5,823,965 to Rasmussen. Rasmussen describes an acoustic reflectometer attached to a flexible closed-ended hose which is introduced into a cavity with the distal end of the hose placed past the zone of the passage to be examined. A transducer converts an activation signal from a signal generator to an excitation signal which is sent into the interior of the hose. A response signal which depends on the local deformation of the hose in the examined zone is picked up by a transducer and subjected to analysis in relation to the excitation signal. An analysis circuit and computer give an image on screen indicating the results of the examination.

Notably, Rasmussen teaches and claims a hose having only a closed distal end. Secondly, Rasmussen teaches and claims determining the internal cross-sectional shape of the hose from the excitation and response signals while the present disclosure directly uses the reflection response signal to determine the location and degree of constrictions within the hose. The internal cross-sectional shape, or the cross-sectional area vs. distance profile, of the hose requires the additional step of calculating the profile using the Ware-Aki or similar algorithm as discussed in U.S. Pat. No. 4,326,416, which is cited by Rasmussen.

SUMMARY OF THE INVENTION

A method for use of acoustic reflectometry in nasogastric enteral access devices is disclosed. The method may include inserting a distal end of a nasogastric enteral access device through the nares a distance into a body and emitting sound waves from a sound generator into a proximal end of a nasogastric enteral access device. The method may also include detecting timings of returning acoustic reflections with at least one sound receiver, the acoustic reflections may include a first acoustic reflection of a first deformation in a wall of the nasogastric enteral access device from a first esophageal sphincter and using a reflectometry device having at least one processor and a memory that is accessible to the processor for analyzing timings of a first acoustic reflection to determine the distance the distal end of a nasogastric enteral access device is inserted into the body.

In some embodiments the method may include determining a length of the nasogastric enteral access device. In some embodiments the method may include determining the distance the distal end of the nasogastric enteral access device is inserted into the body based on the determined length of the nasogastric enteral access device and the timing of the returning acoustic reflections.

In some embodiments first esophageal sphincter is the lower esophageal sphincter. In some embodiments the first esophageal sphincter is the upper esophageal sphincter. In some embodiments, the returning acoustic reflections may include a second acoustic reflection of a second deformation in the wall of the nasogastric enteral access device from a second esophageal sphincter and may also include using the reflectometry device having the at least one processor and the memory that is accessible to the processor for analyzing timings of the returning acoustic reflections to determine a distance the distal end of a nasogastric enteral access device is inserted past the second esophageal sphincter and indicating the distal end of the nasogastric enteral access device is in the stomach when the distal end of the nasogastric enteral access device is the distance passed the second esophageal sphincter.

In some embodiments, the first esophageal sphincter is a lower esophageal sphincter and may include using the reflectometry device having the at least one processor and the memory that is accessible to the processor for analyzing timings of the returning acoustic reflections to determine a distance the distal end of a nasogastric enteral access device is inserted past the lower esophageal sphincter. In some embodiments the method may include indicating that the distal end of the nasogastric enteral access device is in the stomach when the distal end of the nasogastric enteral access device is the distance passed the lower esophageal sphincter.

In some embodiments, determining a constant distance between the first deformation and the second deformation may include detecting a plurality of timings between the first and second acoustic reflections over a time period and comparing the plurality of timings and determining that that timings vary by less than 5% over the time period.

In some embodiments, the nasogastric enteral access device may be advanced or withdrawn within the esophagus or stomach during the time period.

In some embodiments, detecting amplitudes of the returning acoustic reflections with the at least one sound receiver may occur over a time period and include detecting a base and dynamic component of the amplitude over the time period. In some embodiments, the dynamic component coincides with a respiratory cycle of the patient.

In some embodiments, the method may include clearing the nasogastric enteral access device by providing positive pressure into the nasogastric enteral access device to push fluids out the distal end of the nasogastric enteral access device.

A method for use of acoustic reflectometry in nasogastric enteral access devices is disclosed. The method may include inserting a distal end of a nasogastric enteral access device through the nares a distance into a body and emitting sound waves from a sound generator into a nasogastric enteral access device. The method may also include detecting amplitudes and timings of returning acoustic reflections with at least one sound receiver at a plurality positions of the distal end of the nasogastric enteral access device within the body and using a reflectometry device having at least one processor and a memory that is accessible to the processor for analyzing amplitudes and timings of the returning acoustic reflections to detect a positive amplitude deflection in the acoustic reflections at a first position of the distal end of the nasogastric enteral access device within the body, the positive amplitude deflection in the acoustic reflections being from the distal end of the nasogastric enteral access device.

In some embodiments, the method may include indicating, based on the detection of a positive amplitude deflection in the acoustic reflections at a first position of the distal end of the nasogastric enteral access device within the body, that the distal end of the nasogastric enteral access device is above or at the lower esophageal sphincter, the positive amplitude deflection in the acoustic reflections being from the distal end of the nasogastric enteral access device.

In some embodiments, the method may include using the reflectometry device having the at least one processor and the memory that is accessible to the processor for analyzing amplitudes and timings of the returning acoustic reflections to detect a negative amplitude deflection in the acoustic reflections at a second position of the distal end of the nasogastric enteral access device within the body, the second position being further advanced into the body as compared to the first position and the negative amplitude deflection in the acoustic reflections being from the distal end of the nasogastric enteral access device.

In some embodiments, the method may include indicating, based on the detection of a positive amplitude deflection at the first position and the negative amplitude at the second position, that the distal end of the nasogastric enteral access device is within a stomach.

In some embodiments, the detecting may occur as the distal end of the nasogastric enteral access device is advancing in the body. In some embodiments, the detecting occurs while the distal end of the nasogastric enteral access device is stationary within the body.

In some embodiments, the method may include estimating a distance to the lower esophageal sphincter prior to inserting the nasogastric enteral access device into the stomach and indicating, based on the detection and timings of a positive amplitude deflection in the acoustic reflections at a first position of the distal end of the nasogastric enteral access device within the body and the estimated distance to the lower esophageal sphincter, that the distal end of the nasogastric enteral access device is at the lower esophageal sphincter.

In some embodiments, the nasogastric enteral access device comprises a plurality of ports, and the method may include acoustically coupling an acoustic reflectometer, including the sound generator and a sound receiver, to a first of the plurality of ports and occluding a second or more of the plurality of ports not coupled to the sound generator.

In some embodiments, the method may include calibrating the nasogastric enteral access device using a reflectometry device having at least one processor and a memory that is accessible to the processor by determining the amplitude of an acoustic reflection arising from the distal end of the nasogastric enteral access device being open to air.

A method for use of acoustic reflectometry in nasogastric enteral access devices is also disclosed. The method may include estimating a distance to the lower esophageal sphincter prior to inserting the enteral access device into the stomach; inserting a distal end of a nasogastric enteral access device through the nares a distance into a body as indicated by a distance marking on the outside of the nasogastric enteral access device that is visible at the nares and emitting sound waves from a sound generator into a nasogastric enteral access device. The method may also include detecting amplitudes and timings of returning acoustic reflections with at least one sound receiver at a plurality positions of the distal end of the nasogastric enteral access device within the body and using a reflectometry device having at least one processor and a memory that is accessible to the processor for analyzing amplitudes and timings of the returning acoustic reflections to detect a negative amplitude deflection in the acoustic reflections at a first position of the distal end of the nasogastric enteral access device within the body, the negative amplitude deflection in the acoustic reflection being from the distal end of the nasogastric enteral access device. In some embodiments, the first and second negative amplitude deflections may be consecutive.

In some embodiments, the method may include indicating, based on the detection of the first and second negative amplitude deflections at the first position, that the distal end of the nasogastric enteral access device is within a trachea.

In some embodiments, the method may include indicating, based on the detection of a negative amplitude deflection at a first position and the insertion distance of the first position being less than the estimated distance to the lower esophageal sphincter, that the distal end of the nasogastric enteral access device is within a trachea.

In some embodiments, the method may include indicating that the distal end of the nasogastric enteral access device is within a trachea upon detection of a second negative amplitude deflection in the acoustic reflections.

A system for use of acoustic reflectometry in nasogastric enteral access devices is also disclosed. The system may include a nasogastric enteral access device and a sound generator acoustically coupled to the proximal end of a nasogastric enteral access device to emit sound waves into the nasogastric enteral access device. The system may also include at least one sound receiver to detect timings of returning acoustic reflections, the acoustic reflections including a first acoustic reflection of a first deformation in a wall of the nasogastric enteral access device from a first esophageal sphincter and a reflectometry device having at least one processor and a memory that is accessible to the processor for analyzing timings of the returning acoustic reflections to determine the distance the distal end of a nasogastric enteral access device is inserted into the body. In some embodiments, the reflectometry device is configured to determine the distance the distal end of the nasogastric enteral access device is inserted into the body based on a length of the nasogastric enteral access device and the timing of the first acoustic reflection.

In some embodiments, the first esophageal sphincter is a lower esophageal sphincter; and the reflectometry device is configured to indicate that the distal end of the nasogastric enteral access device is in the stomach when the distal end of the nasogastric enteral access device is a distance passed the lower esophageal sphincter.

In some embodiments, the returning acoustic reflections include a second acoustic reflection of a second deformation in the wall of the nasogastric enteral access device from a second esophageal sphincter and the reflectometry device may be configured to determine the distal end of the nasogastric enteral access device is in the stomach when the distal end of the nasogastric enteral access device is a distance passed the second esophageal sphincter.

In some embodiments, the reflectometry device may configured to determine a constant distance between the first deformation and the second deformation by detecting a plurality of timings between the first and second acoustic reflections over a time period and comparing the plurality of timings and determining that that timings vary by less than 5% over the time period.

In some embodiments, the reflectometry device may be configured to detect amplitudes of the returning acoustic reflections with the at least one sound receiver over a time period and detect a base and dynamic component of the amplitude over the time period.

A system for use of acoustic reflectometry in nasogastric enteral access devices is also disclosed. The system may include a nasogastric enteral access device and a sound generator to emit sound into the nasogastric enteral access device. The system may include at least one sound receiver to detect amplitudes and timings of returning acoustic reflections at a plurality positions of a distal end of the nasogastric enteral access device within a body and a reflectometry device having at least one processor and a memory that is accessible to the processor configured to analyze amplitudes and timings of the returning acoustic reflections and to detect a positive amplitude deflection in the acoustic reflections at a first position of the distal end of the nasogastric enteral access device within the body, the positive amplitude deflection in the acoustic reflections being from the distal end of the nasogastric enteral access device.

In some embodiments, the reflectometry device may be configured to indicate, based on the detection of a positive amplitude deflection in the acoustic reflections at a first position of the distal end of the nasogastric enteral access device within the body, that the distal end of the nasogastric enteral access device is above or at the lower esophageal sphincter, the positive amplitude deflection in the acoustic reflections being from the distal end of the nasogastric enteral access device.

In some embodiments, the reflectometry device may be configured to analyze amplitudes and timings of the returning acoustic reflections to detect a negative amplitude deflection in the acoustic reflections at a second position of the distal end of the nasogastric enteral access device within the body, the second position being further advanced into the body as compared to the first position and the negative amplitude deflection in acoustic reflections being from the distal end of the nasogastric enteral access device.

In some embodiments, the reflectometry device is configured to indicate, based on the detection of a positive amplitude deflection at the first position and the negative amplitude at the second position, that the distal end of the nasogastric enteral access device is within a stomach.

In some embodiments, the sound receiver is configured to detect the reflections as the distal end of the nasogastric enteral access device advances in the body. In some embodiments, the sound receiver is configured to detect the reflections while the distal end of the nasogastric enteral access device is stationary within the body.

In some embodiments, the reflectometry device is configured with an estimate of a distance to the lower esophageal sphincter prior to inserting the nasogastric enteral access device into the stomach and to indicate, based on the detection and timings of a positive amplitude deflection in the acoustic reflections at a first position of the distal end of the nasogastric enteral access device within the body and the estimated distance to the lower esophageal sphincter, that the distal end of the nasogastric enteral access device is at the lower esophageal sphincter.

In some embodiments, the nasogastric enteral access device comprises a plurality of ports, and the acoustic reflectometer is acoustically coupled to a first of the plurality of ports and a second or more of the plurality of ports not coupled to the sound generator are occluded.

A system for use of acoustic reflectometry in nasogastric enteral access devices is disclosed. The system may include a nasogastric enteral access device having a proximal end and a distal end and a sound generator to emit sound waves into a nasogastric enteral access device. The system may also include at least one sound receiver to detect amplitudes and timings of returning acoustic reflections a plurality positions of the distal end of the nasogastric enteral access device within a body and a reflectometry device having at least one processor and a memory that is accessible to the processor for analyzing amplitudes and timings of the returning acoustic reflections to detect first and second negative amplitude deflections in the acoustic reflections at a first position of the distal end of the nasogastric enteral access device within the body.

In some embodiments, the first and second negative amplitude deflections are consecutive.

In some embodiments, the reflectometry device is configured to indicate, based on the detection of the first and second negative amplitude deflections at the first position, that the distal end of the nasogastric enteral access device is within a trachea.

In some embodiments, the reflectometry device is further configured to indicate, based on the detection of a negative amplitude deflection at a first position and the insertion distance of the first position being less than an estimated distance to the lower esophageal sphincter, that the distal end of the nasogastric enteral access device is within a lower airway.

In some embodiments, the reflectometry device is configured to indicate that the distal end of the nasogastric enteral access device is within a trachea upon detection of a second negative amplitude deflection in the acoustic reflections, the first negative amplitude deflection being from the distal end of the nasogastric enteral access device and the second negative amplitude deflection being from a location within an airway, distal to the distal end of the nasogastric enteral access device.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The features and advantages of this disclosure, and the manner of attaining them, will be more apparent and better understood by reference to the following descriptions of the disclosed methods and systems, taken in conjunction with the accompanying drawings, wherein.

DETAILED DESCRIPTION OF THE INVENTION

Figure 1:
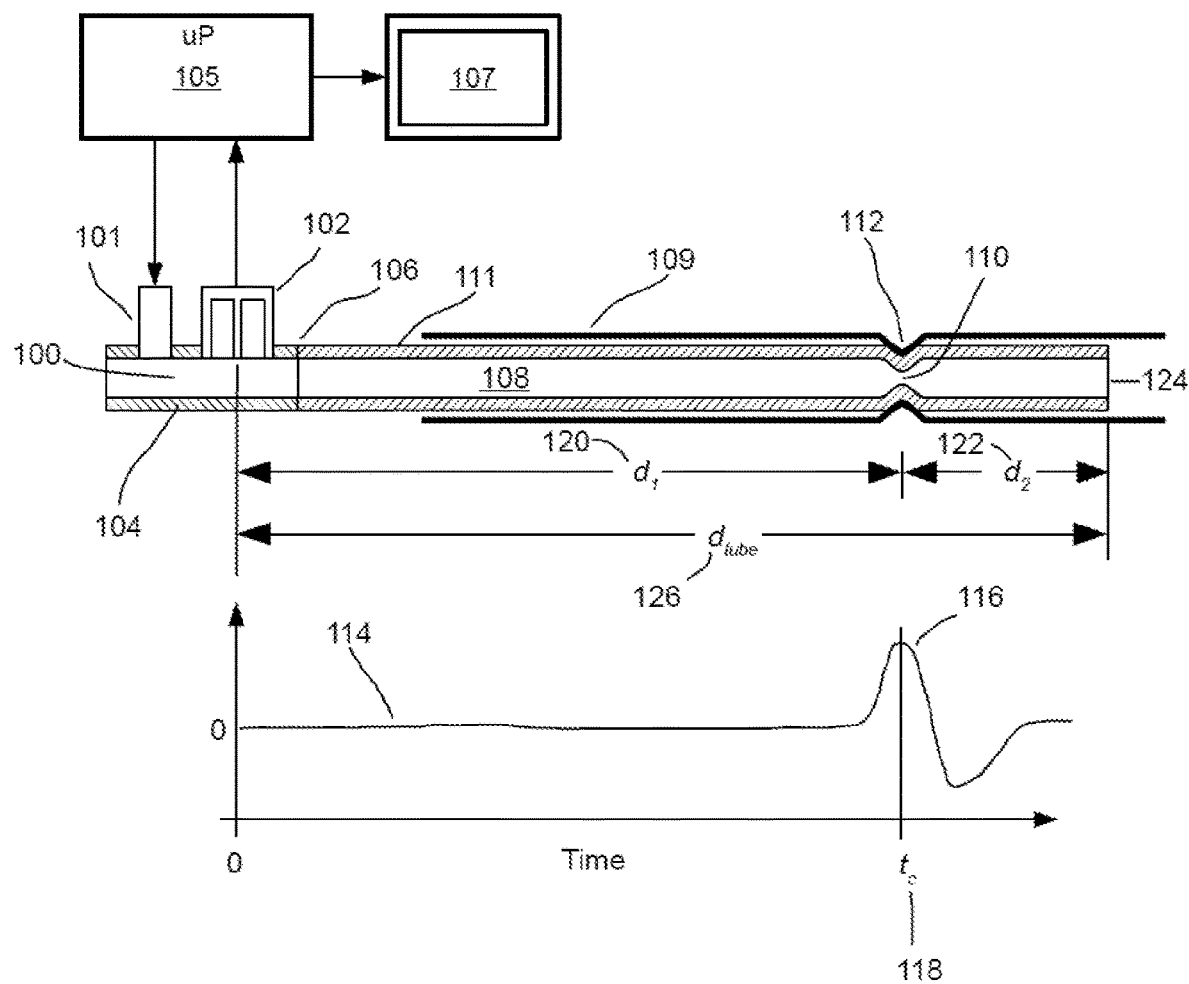
FIG. 1 shows a drawing of the acoustic reflectometry system connected to a tube which is inserted into a body cavity containing a constriction.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The present disclosure includes disclosure of devices and methods for verifying the proper position of catheters in a human body by means of acoustic reflectometry. The device comprises a sound source, one or more sound receivers, and a tube with compliant walls and open distal end to be introduced through an entrance to a body cavity. The sound source and receiver(s) are coupled to the proximal end of the tube. The device includes a processor for causing the sound source to generate an acoustic excitation signal. The processor then processes the acoustic signals sensed by the sound receiver(s), generates an approximation of the acoustic impulse response of the tube, and analyzes the acoustic impulse response to determine the position of the tube in the body cavity.

The embodiment of the present disclosure shown in FIG. 1 uses an acoustic reflectometry device 100 which includes a sound generator 101 and one or more sound receivers 102 embedded into the wall of a wave tube 104. The sound generator 101 and sound receiver(s) 102 are in communication with a processor 105 with attached display 107. Two sound receivers may be used as described in Wodicka U.S. Pat. No. 6,705,319 for a compact acoustic reflectometer that provides the means to separate the incident and reflected acoustic signals and thereby simplifies the calculation of an approximation of the acoustic impulse response (reflection waveform) 114. The acoustic impulse response 114 can be calculated using an excitation signal from the sound generator 101 that comprises acoustic energy over the frequencies of interest (e.g. 0.1-10 kHz), including a broadband sound pulse or white noise. The distal wave tube end 106 is coupled to the proximal end of an open-ended NG tube 108. When NG tube 108 is inserted into a body cavity 109, there may arise one or more local deformations 110 of the tube wall 111 due to a narrowed or constricted region 112 within the passageway 109 such as from a sphincter or other structure that applies pressure on the compliant tube wall 111. The corresponding acoustic impulse response 114 derived by the processor from the sound receiver 102 signals contains a sound reflection 116 that arises from the constriction 110 within the tube 108. The time delay 118 ($t_c$) of the sound reflection 116 and the speed of sound c in air are used to calculate a first distance 120 ($d_1$) between the sound receiver (s) 102 and the tube constriction 110 using $$d = \frac{ct_c}{2},$$

where the 2 in the divisor accounts for the round trip travel of the sound between the sound receiver(s) 102 and tube constriction 110. A second distance 122 ($d_2$) between the constriction 110 and the distal tube end 124 is calculated by subtracting the first distance 120 ($d_1$) from the tube length 126 ($d_{tube}$). The tube length 126 may either be known in advance, provided by the user, or determined during a calibration step to estimate the tube length 126. The calibration step to estimate the tube length 126 could consist of obtaining an acoustical measurement prior to inserting the tube 108 into the body passageway 109 and calculating tube length 126 by using the time delay of the sound reflection from the distal tube end 124 obtained from the corresponding acoustic reflection waveform 114.

Figure 2:
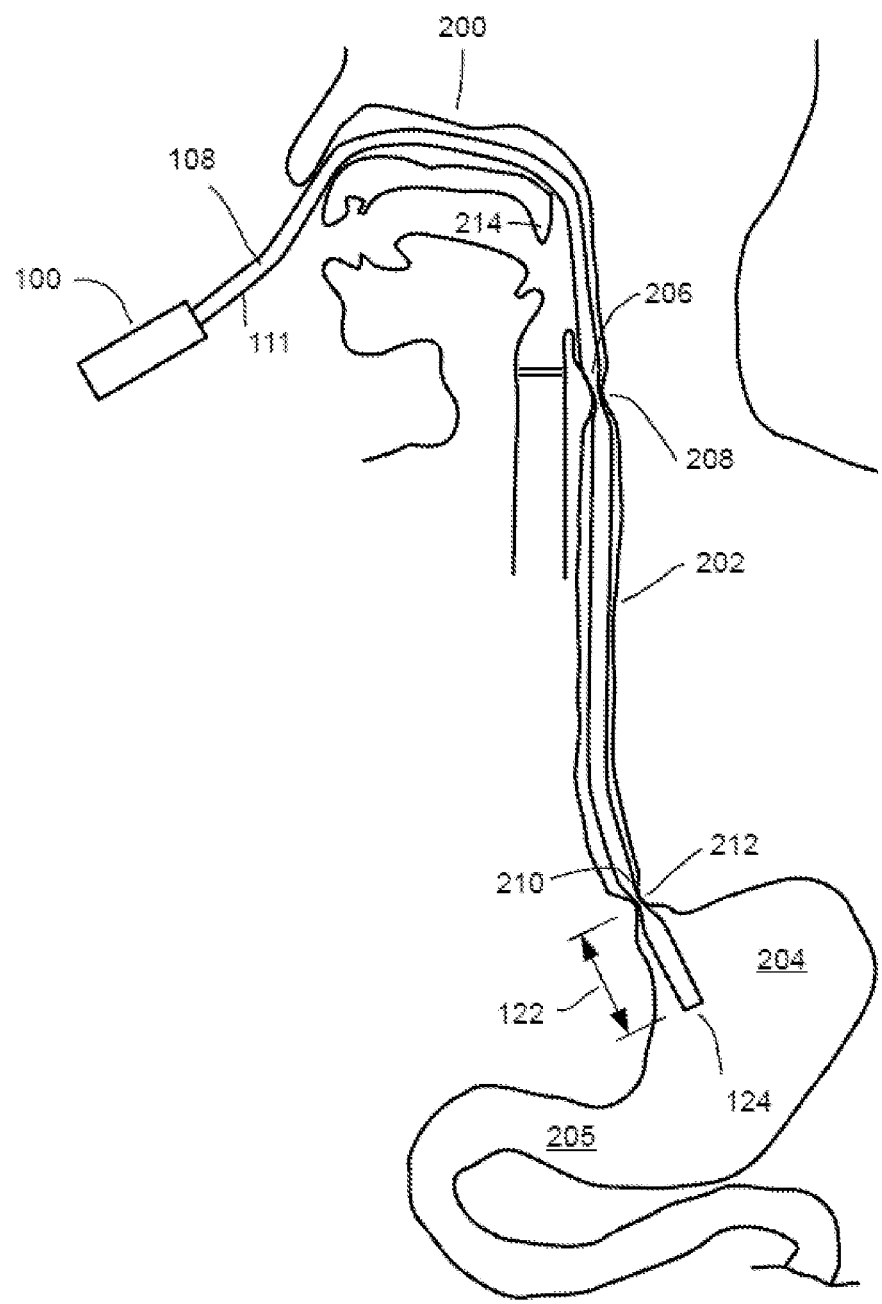
FIG. 2 illustrates the placing of an NG tube with attached acoustic reflectometer into body passages leading to the stomach.

FIG. 2 depicts one embodiment of the acoustic reflectometer 100 attached to NG tube 108 which is inserted into a body cavity comprising a nasal cavity 200, esophagus 202, and stomach 204. The NG tube 108 may have a first local deformation 206 at the upper esophageal sphincter (UES) 208 and a second local deformation 210 at the lower esophageal sphincter (LES) 212. The locations of the first and second local deformations 206 and 210 along the NG tube 108 are estimated using the delay times of their respective sound reflections using the equation previously described. The distance 122 by which the distal tube end 124 is past the LES 212 extending into the stomach 204 is calculated as previously described using the distance of the second local deformation 210 and the NG tube length 126 (from FIG. 1). This distance 122 can be used to guide the position of the distal tube end 124 into the desired location in or past the stomach 204. For example, if it is desired to position the tube end 124 through the stomach 204 into the duodenum 205, then distance 122 as reported by the system can be increased an amount determined by the user to put the tube end 124 approximately into the duodenum 205.

It is possible that fluids such as from the nasal passageway 200, esophagus 202, stomach 204, or elsewhere, or any combination thereof, may enter the distal tube end 124 and result in a false positive detection of a constriction of the NG tube wall 111. As a preventative measure, it may be necessary to connect a device such as an air filled syringe to the wave tube proximal end 212 and provide a bolus of positive pressure air with the syringe to flow air though the NG tube and push fluids through the NG tube 108 and out of the distal tube end 124.

Positive confirmation of the distal tube end 124 into the stomach 204 is provided when the device detects the second local deformation 210 arising from the LES 212 constricting the tube wall 111. An additional positive confirmation of the NG tube 108 traversing the length of the esophagus 202 with the distal tube end 124 located past the LES 212 is the presence of the first and second local deformations 206 and 210 that arise from the UES 208 and LES 212, respectively. Further confirmation that the NG tube 108 is inserted fully through the esophagus 202 is the observation of a constant distance between the deformations 206 and 210 in the NG tube 108 as it is advanced into or withdrawn from the stomach 204. A constant distance may be determined based on multiple distance observations being within a threshold value of each other. For example, the distance variance may be within 1%, 5%, or 10% of each other, or within 0.5 cm, 1 cm, 2 cm, or 3 cm of each other.

It is possible that additional structures within the body cavities traversed by the NG tube 108 may cause temporary local deformations in the tube wall 111. These structures may include the nasopharynx 214 which may close voluntarily by the patient or involuntarily during swallowing. There may also be other structures within the upper airway that may cause local deformations in the tube wall 111.

The lower esophageal sphincter 212 has several characteristics that allow discrimination of the deformation of the tube wall 111 due to the LES 212 from deformation due to other structures. The LES base pressure is typically between 6-20 mmHg and has a dynamic component that increases 15-20 mmHg during the inspiratory phase of tidal inspiration, and with forceful inspiration the increase can be 100-150 mmHg. The dynamic component may be periodic. This varying pressure on the tube wall 111 causes the tube wall 111 deformation to also vary such that the degree of constriction of the NG tube 108 is correlated to the pressure. This varying NG tube constriction due to the LES 212 can be observed as a change in amplitude of the sound reflection 116 (FIG. 1) arising from the constriction. If the acoustic reflectometry device 100 is configured to collect a complete acoustic reflection waveform 114 multiple times per second, then the change in constriction size as a function of time (over seconds) can be observed and used as a positive confirmation that the constriction in the NG tube 108 is from the LES 212.

Another characteristic of the LES 212, as well as the UES 208, is the relaxation that occurs during swallowing. During swallowing, the LES relaxation lasts 6-10 seconds. Again, if the acoustic reflectometry device 100 is configured to collect a complete acoustic reflection waveform 116 multiple times per second, then the change in constriction size as a function of time (over seconds) can be observed and used to confirm the presence of the relaxation period that is synchronized with swallowing. If this relaxation period is observed, then it can be used as another indicator of positive confirmation that the constriction in the NG tube 108 is from the LES 212.

The abovementioned characteristics of the LES 212 that are observable in the acoustic reflection signal 114 may be used individually or in some combination to positively confirm that the NG distal tube end 124 is extended past the LES 212 into the stomach 204.

Figure 3:
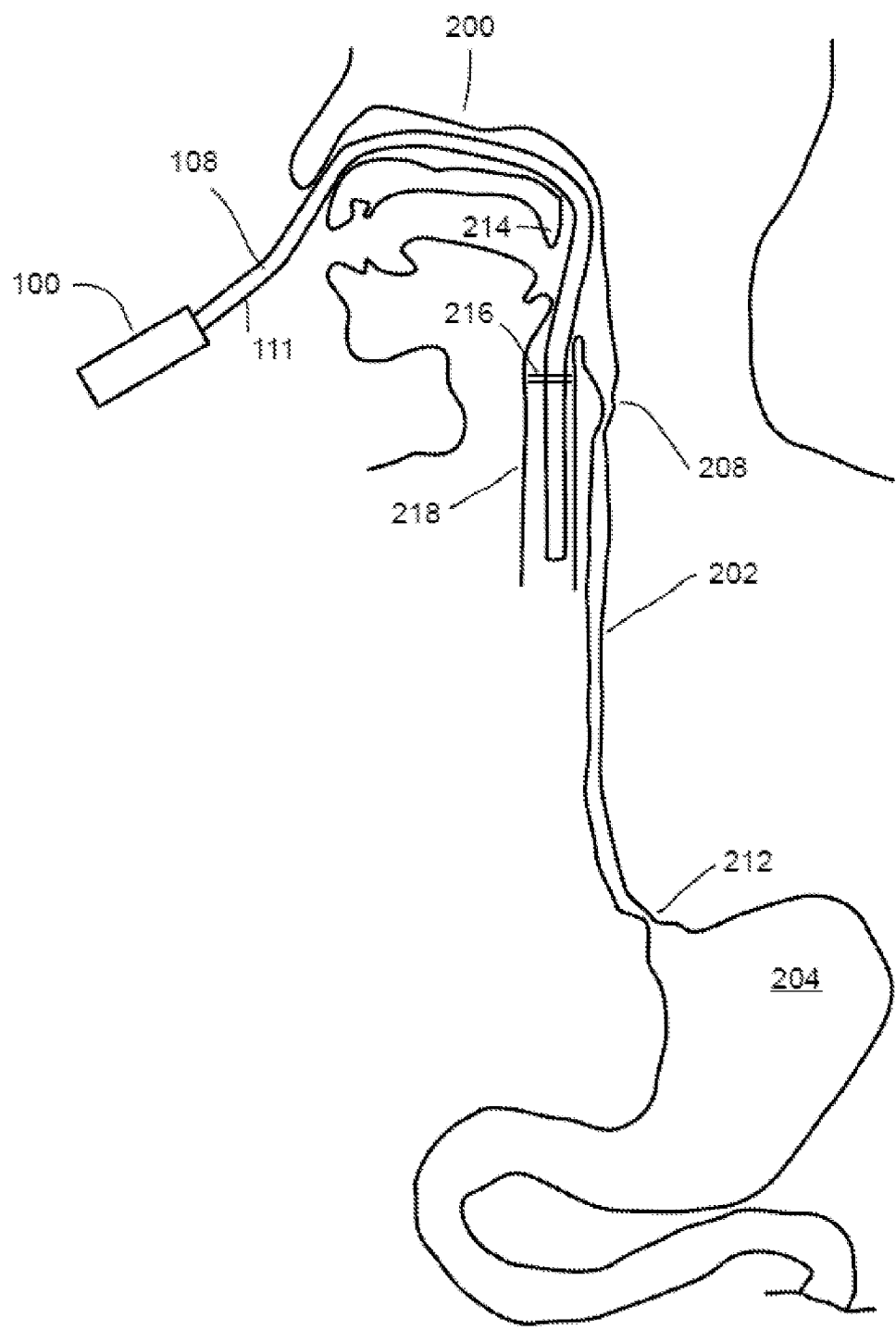
FIG. 3 illustrates the placing of an NG tube with attached acoustic reflectometer into body passages leading to the lungs.

FIG. 3 depicts the NG tube 108 erroneously advanced past the vocal folds 216 into the trachea 218. In this case, the tube wall deformations due to compression by the UES 208 and LES 212, respectively, along with their individual characteristics discussed above, will not be observed. It is possible that closure of the vocal folds 216 may pinch the tube 108 and be detected as a constriction by the acoustic reflectometer 100, but this constriction will not have the same characteristics as those arising from the structures 208 and 212 within the esophagus 202. The lower airway may be the airway below the vocal folds.

Figure 4:
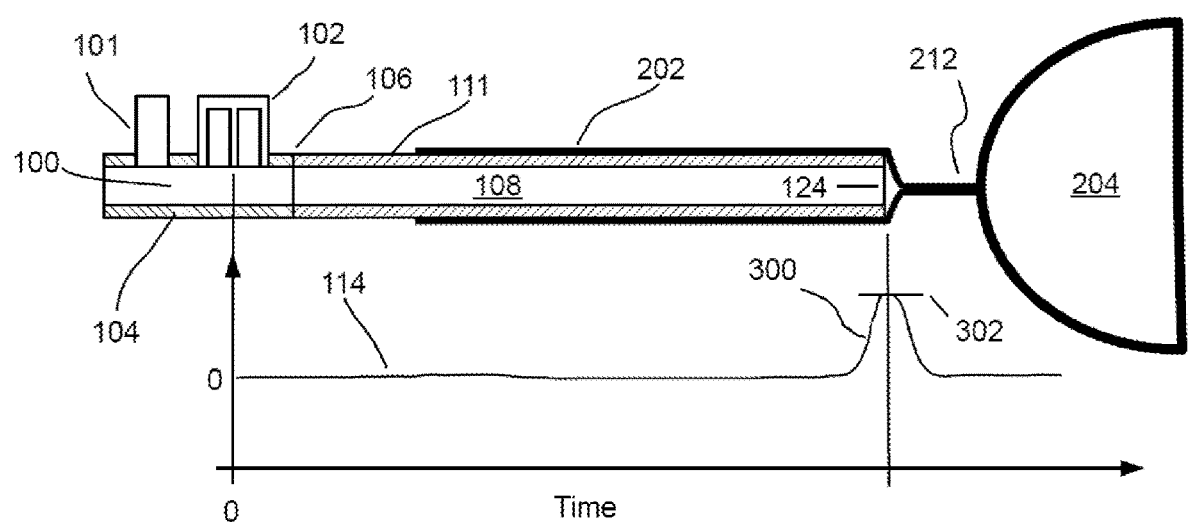
FIG. 4 shows a drawing of the acoustic reflectometry device connected to a tube with the distal tube end inserted into an esophagus.

Referring to FIG. 4, if the NG tube wall 111 is not sufficiently compliant to deform from a narrowed or constricted region within the esophagus 202, then there are alternate means to verify that the distal tube end 124 is past the LES 212 and extending into the stomach 204.

The acoustic reflection 300 arising from the distal tube end 124 is related to the cross-sectional areas of the catheter lumen and the passageway immediately around the opening of the distal tube end 124. This relationship is described as $$S_1 = \left(\frac{1-R}{1+R}\right) S_0 \qquad (1)$$

where $S_0$ and $S_1$ are the respective cross-sectional areas of the catheter lumen and passageway immediately around the opening of the distal tube end 124, and R is the dimensionless reflection coefficient ($-1 \leq R \leq 1$) related to the amplitude 302 of the acoustic reflection 300 arising from the distal tube end 124. The value of R for the acoustic reflection 300 can be determined by measuring the acoustic reflection amplitude, $A_{cal}$, arising for a known $S_0$ and $S_1$ during a calibration step and using this value to calculate R. For example, upon connection of the device 100 to the NG tube 108 and prior to insertion of the tube 108 into the patient, an acoustic measurement can be obtained while the distal tube end 124 is open to air (case where $S_1 \approx \infty$). The amplitude of the resulting acoustic reflection arising from the distal tube end 124, $A_{cal}$, would represent the case for $R_{open} = -1$. Then, all subsequent amplitude measurements, A 302, of the acoustic reflection 300 arising from the distal tube end 124 can be converted into a reflection coefficient using $$R = R_{open} \frac{A}{A_{cal}} \qquad (2)$$

Then R may be applied to (1) to estimate the cross-sectional area, $S_1$, of the passageway immediately around the distal tube end 124.

In an alternate embodiment, $A_{cal}$ may be obtained a priori for catheters of a specified diameter, length, manufacturer, and model, and stored within a lookup table. It may be necessary to know the manufacturer and model of a catheter because the sound attenuation through the catheter may be affected by the catheter wall mechanical properties which may vary between manufacturers and models of catheters. In yet another embodiment, $A_{cal}$ may be calculated from an equation, $A_{cal}(d, l)$ that is empirically derived using data points for $A_{cal}$ that are obtained experimentally over varying catheter diameters, d, and lengths, l, (and manufacturers and models, if necessary).

Figure 5:
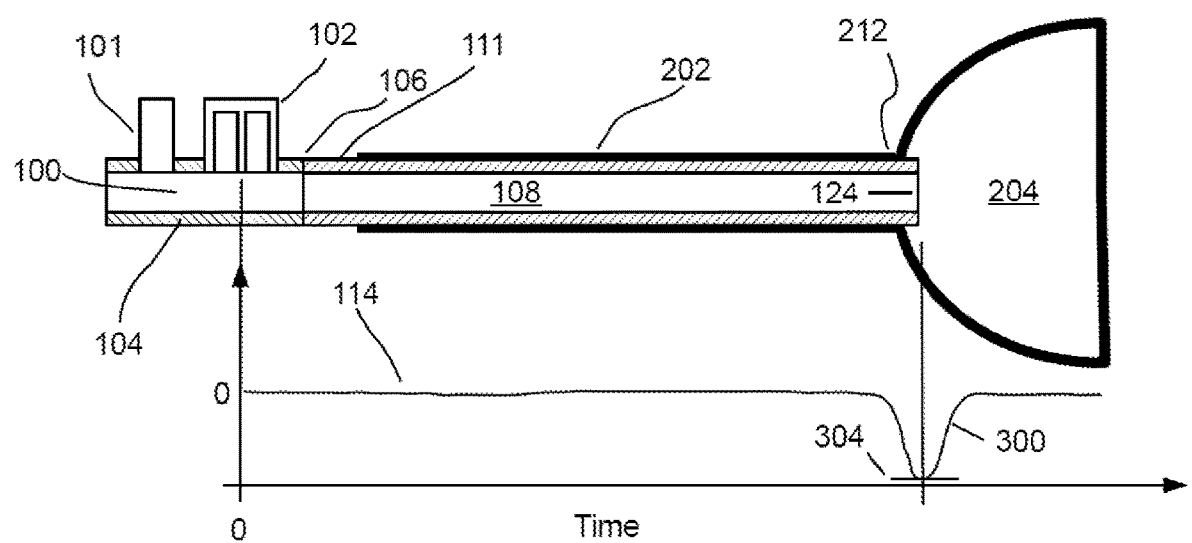
FIG. 5 shows a drawing of the acoustic reflectometry device connected to a tube with the distal tube end inserted into a stomach.

Again, referring to FIG. 4, if the distal tube end 124 is located proximally to or at the LES 212 within the esophagus 202, then the esophageal tissue will close off the distal tube end 124 by virtue of the tissue's collapsible nature over the tip opening and the resulting acoustic reflection 300 arising from the closed distal tube end 124 will be detected as a positive deflection 302 in the reflection waveform 114. In contrast, as shown in FIG. 5, if the distal tube end 124 is located distal to the LES 212 within the stomach 204, then the distal tube end 124 will be open into the cavity formed by the stomach 204, and the resulting acoustic reflection 300 arising from the open distal tube end 124 will be detected as a negative deflection 304 in the reflection waveform 114.

In some embodiments, prior to insertion, the proper insertion distance of the NG tube 108 into a patient is estimated using a commonly employed method of measuring the total distance from the nose to the ear lobe to the xiphoid process. During advancement of the NG tube into the body, the timings and amplitudes of the reflections of the waveform 114 are detected. In some embodiments, placement of the distal end of the NG tube at the LES may occur based on the detection and timings of a positive amplitude deflection in the acoustic reflections at a first position of the distal end of the nasogastric enteral access device within the body, for example, when the distal end of the NG tube is at the LES, and the estimated distance to the LES, that the distal end of the nasogastric enteral access device is at the lower esophageal sphincter.

By using the markings showing distance from the distal tube end 124 to the nares or mouth, typically provided along the outside of the NG tube 108, one can note the presence or absence of a collapsed cavity (e.g. the esophagus, stomach, or trachea) around the distal tube end 124 while advancing the NG tube 108 by detecting the amplitude and polarity of the reflection wave 300 arising from the distal tube end 124. Prior to insertion, the proper insertion distance of the NG tube 108 into a patient is estimated using a commonly employed method of measuring the total distance from the nose to the ear lobe to the xiphoid process. During insertion of the NG tube 108, guidance of the distal tube end 124 is provided by detecting the amplitude and timings of an acoustic reflection 300 that has either a positive deflection (collapsed esophagus) or small negative deflection (partially collapsed esophagus) while the distal tube end is advancing in the esophagus 202. When the distal tube end 124 enters the stomach 204, this is confirmed by detecting a large negative deflection 304 arising from the distal tube end 124. The estimated proper insertion distance should approximately agree with the insertion distance at which the cavity around the distal tube end 124 transitioned from collapsed or partially collapsed (esophagus) to open (stomach).

Figure 6:
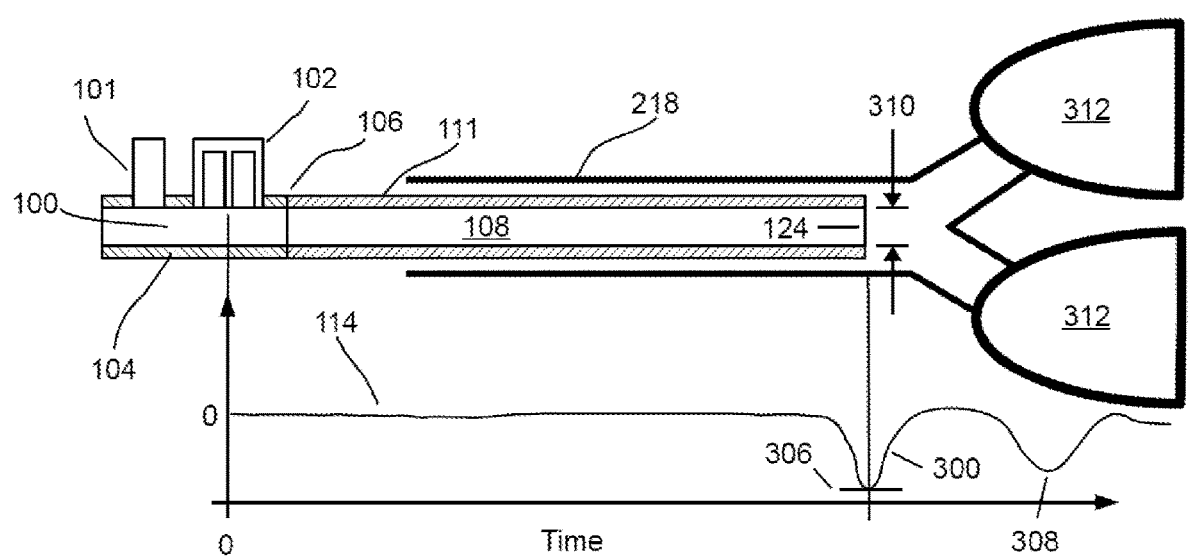
FIG. 6 shows a drawing of the acoustic reflectometry device connected to a tube with the distal tube end inserted into a trachea.

Improper placement of the NG tube 108 into the trachea 218 (FIG. 6) is indicated by detecting an acoustic reflection 300 that has a significant negative deflection 306 (the trachea) at an insertion distance of the NG tube 108 significantly smaller than the estimated proper insertion distance to the stomach. This small insertion distance is due to the distal tube end 124 entering the trachea 218 where it would have instead started entering the esophagus just below the upper airway if proper placement had occurred. In addition, if the NG tube diameter 310 is of comparable size to that of the trachea 218, there may be adequate acoustic energy transmission between the tube 108, trachea 218, and airways 312 to observe the characteristic echo 308 from the airways that arises from the branching generations where the total cross-sectional area grows rapidly. The presence of this negative going airway echo 308 in the acoustic reflection waveform 114 may provide an additional confirmation that the distal tube end 124 is improperly placed in the trachea 218.

The proximal ports for NG tubes can vary in number depending on the intended use for the tube. For example, some NG tubes may have two or more ports to allow administration of both food and medications simultaneously. If an NG tube is used that contains two or more ports, it may be necessary to occlude all of the ports with plugs except for the one acoustically coupled to the acoustic reflectometer. This will prevent extraneous acoustic reflections arising from the ports from interfering with the reflections arising from within the NG tube and cavities in which the tube is inserted. In one embodiment, the plug diameters are made to fit the inner diameter of the ports and the plug lengths are made to extend into the port far enough to completely fill the port and, therefore, minimize the increase in cross-sectional area of the NG tube resulting from the port. In another embodiment, a calibration procedure is used to measure the reflection echoes arising from the ports in their open or closed states and remove their effects on the entire acoustic reflection signal either through methods such as subtraction or deconvolution.

While this disclosure has been described as having preferred designs, the apparatus and methods according to the present disclosure can be further modified within the scope and spirit of this disclosure. This application is therefore intended to cover any variations, uses, or adaptations of the disclosure using its general principles. For example, any methods disclosed herein and in the appended claims represent one possible sequence of performing the steps thereof. A practitioner may determine in a particular implementation that a plurality of steps of one or more of the disclosed methods may be combinable, or that a different sequence of steps may be employed to accomplish the same results. Each such implementation falls within the scope of the present disclosure as disclosed herein and in the appended claims. Furthermore, this application is intended to cover such departures from the present disclosure as come within known or customary practice in the art to which this disclosure pertains.

What is claimed is:

1. A method for use of acoustic reflectometry in nasogastric enteral access devices, the method comprising:
   inserting a distal end of a nasogastric enteral access device through a naris a distance into a body;
   emitting sound waves from a sound generator into a proximal end of the nasogastric enteral access device;
   detecting timings of returning acoustic reflections with at least one sound receiver, the acoustic reflections including a first acoustic reflection of a first deformation in a wall of the nasogastric enteral access device from a first esophageal sphincter, wherein the returning acoustic reflections include a second acoustic reflection of a second deformation in the wall of the nasogastric enteral access device from a second esophageal sphincter;
   using a reflectometry device having at least one processor and a memory that is accessible to the processor for analyzing timings of the returning acoustic reflections to determine the distance the distal end of the nasogastric enteral access device is inserted past the second esophageal sphincter; and
   indicating the distal end of the nasogastric enteral access device is in the stomach when the distal end of the nasogastric enteral access device is the distance passed the second esophageal sphincter.

2. The method of claim 1, further comprising:
   determining a length of the nasogastric enteral access device.

3. The method of claim 2, wherein determining the distance the distal end of the nasogastric enteral access device is inserted into the body is based on the determined length of the nasogastric enteral access device and the timing of the first acoustic reflection.

4. The method of claim 3, wherein the first esophageal sphincter is the lower esophageal sphincter.

5. The method of claim 3, wherein the first esophageal sphincter is the upper esophageal sphincter.

6. A method for use of acoustic reflectometry in nasogastric enteral access devices, the method comprising:
   inserting a distal end of a nasogastric enteral access device through a naris a distance into a body;
   emitting sound waves from a sound generator into a proximal end of the nasogastric enteral access device;
   detecting timings of returning acoustic reflections with at least one sound receiver, the acoustic reflections including a first acoustic reflection of a first deformation in a wall of the nasogastric enteral access device from a lower esophageal sphincter;
   using the reflectometry device having the at least one processor and the memory that is accessible to the processor for analyzing timings of the returning acoustic reflections to determine a distance the distal end of the nasogastric enteral access device is inserted past the lower esophageal sphincter; and
   indicating that the distal end of the nasogastric enteral access device is in the stomach when the distal end of the nasogastric enteral access device is the distance passed the lower esophageal sphincter.

7. The method of claim 1, further comprising:
   determining a constant distance between the first deformation and the second deformation by:
   detecting a plurality of timings between the first and second acoustic reflections over a time period; and
   comparing the plurality of timings and determining that the plurality of timings vary by less than 5% over the time period.

8. The method of claim 7, wherein the nasogastric enteral access device is advanced or withdrawn within the esophagus or stomach during the time period.

9. The method of claim 1, further comprising:
   detecting amplitudes of the returning acoustic reflections with the at least one sound receiver over a time period;
   detecting a base component and a dynamic component of the amplitude over the time period.

10. The method of claim 9, wherein the dynamic component coincides with a respiratory cycle of the patient.

11. The method of claim 1, further comprising:
    clearing the nasogastric enteral access device by providing positive pressure into the nasogastric enteral access device to push fluids out the distal end of the nasogastric enteral access device.

12. A method for use of acoustic reflectometry in nasogastric enteral access devices, the method comprising:
    estimating a distance to the lower esophageal sphincter from a naris;
    inserting a distal end of a nasogastric enteral access device through the naris a distance into a body;
    emitting sound waves from a sound generator into the nasogastric enteral access device;
    detecting amplitudes and timings of returning acoustic reflections with at least one sound receiver at a plurality of positions of the distal end of the nasogastric enteral access device within the body;
    using a reflectometry device having at least one processor and a memory that is accessible to the processor for analyzing amplitudes and timings of the returning acoustic reflections to detect a positive amplitude deflection in the acoustic reflections at a first position of the distal end of the nasogastric enteral access device within the body, the positive amplitude deflection in the acoustic reflections being from the distal end of the nasogastric enteral access device; and
    indicating, based on the detection and timings of the positive amplitude deflection in the acoustic reflections at the first position of the distal end of the nasogastric enteral access device within the body and the estimated distance to the lower esophageal sphincter, that the distal end of the nasogastric enteral access device is at the lower esophageal sphincter.

13. The method of claim 12, further comprising:
    indicating, based on the detection of the positive amplitude deflection in the acoustic reflections at the first position of the distal end of the nasogastric enteral access device within the body, that the distal end of the nasogastric enteral access device is above or at the lower esophageal sphincter, the positive amplitude deflection in the acoustic reflections being from the distal end of the nasogastric enteral access device.

14. The method of claim 12, further comprising:
    using the reflectometry device having the at least one processor and the memory that is accessible to the processor for analyzing amplitudes and timings of the returning acoustic reflections to detect a negative amplitude deflection in the acoustic reflections at a second position of the distal end of the nasogastric enteral access device within the body, the second position being further advanced into the body as compared to the first position and the negative amplitude deflection in the acoustic reflections being from the distal end of the nasogastric enteral access device.

15. The method of claim 14, further comprising:
    indicating, based on the detection of the positive amplitude deflection at the first position and the negative amplitude deflection at the second position, that the distal end of the nasogastric enteral access device is within a stomach.

16. The method of claim 12, wherein the detecting occurs as the distal end of the nasogastric enteral access device is advancing in the body.

17. The method of claim 12, wherein the detecting occurs while the distal end of the nasogastric enteral access device is stationary within the body.

18. A system for use of acoustic reflectometry in nasogastric enteral access devices, the system comprising:
    a nasogastric enteral access device;
    a sound generator to emit sound into the nasogastric enteral access device;
    at least one sound receiver to detect amplitudes and timings of returning acoustic reflections at a plurality of positions of a distal end of the nasogastric enteral access device within a body; and
    a reflectometry device having at least one processor and a memory that is accessible to the processor configured to analyze amplitudes and timings of the returning acoustic reflections and to detect a positive amplitude deflection in the acoustic reflections at a first position of the distal end of the nasogastric enteral access device within the body, the positive amplitude deflection in the acoustic reflections being from the distal end of the nasogastric enteral access device, wherein the reflectometry device is configured with an estimate of a distance to the lower esophageal sphincter from a naris and to indicate, based on the detection and timings of the positive amplitude deflection in the acoustic reflections at the first position of the distal end of the nasogastric enteral access device within the body and the estimated distance to the lower esophageal sphincter, that the distal end of the nasogastric enteral access device is at the lower esophageal sphincter.

19. The system of claim 18, wherein:
the reflectometry device configured to indicate, based on the detection of the positive amplitude deflection in the acoustic reflections at the first position of the distal end of the nasogastric enteral access device within the body, that the distal end of the nasogastric enteral access device is above or at the lower esophageal sphincter, the positive amplitude deflection in the acoustic reflections being from the distal end of the nasogastric enteral access device.

20. A system for use of acoustic reflectometry in nasogastric enteral access devices, the system comprising:
a nasogastric enteral access device having a proximal end and a distal end;
a sound generator to emit sound waves into the nasogastric enteral access device;
at least one sound receiver to detect amplitudes and timings of returning acoustic reflections a plurality of positions of the distal end of the nasogastric enteral access device within a body; and
a reflectometry device having at least one processor and a memory that is accessible to the processor for analyzing amplitudes and timings of the returning acoustic reflections to detect a negative amplitude deflection in the acoustic reflections at a first position of the distal end of the nasogastric enteral access device within the body, the negative amplitude deflection in the acoustic reflections being from the distal end of the nasogastric enteral access device, wherein the reflectometry device is configured to indicate, based on the detection of the negative amplitude deflection at the first position and the insertion distance of the first position being less than an estimated distance to the lower esophageal sphincter from a naris, that the distal end of the nasogastric enteral access device is within a lower airway.

21. The system of claim 20, wherein:
the reflectometry device is configured to indicate that the distal end of the nasogastric enteral access device is within a trachea upon detection of a second negative amplitude deflection in the acoustic reflections, the first negative amplitude deflection being from the distal end of the nasogastric enteral access device and the second negative amplitude deflection being from a location within an airway, distal to the distal end of the nasogastric enteral access device.

* * * * *